(12) United States Patent
Coveney et al.

(10) Patent No.: US 7,338,977 B2
(45) Date of Patent: Mar. 4, 2008

(54) ANTI-VIRAL COMPOUNDS

(75) Inventors: Donal Coveney, Dublin (IE); Benjamin Costello, Dublin (IE)

(73) Assignee: Aids Care Pharma Limited, Dublin (IE)

( * ) Notice: Subject to any disclaimer, the term of this patent is extended or adjusted under 35 U.S.C. 154(b) by 0 days.

(21) Appl. No.: 10/722,060

(22) Filed: Nov. 25, 2003

(65) Prior Publication Data
US 2005/0113454 A1   May 26, 2005

(51) Int. Cl.
*A61K 31/19*   (2006.01)
*A61K 31/05*   (2006.01)
*C07C 63/33*   (2006.01)

(52) U.S. Cl. .................. 514/569; 514/732; 562/491; 562/492

(58) Field of Classification Search ................ 514/130, 514/510, 569, 732; 562/491, 492
See application file for complete search history.

(56) References Cited

FOREIGN PATENT DOCUMENTS

| WO | WO 95/19974 | * | 7/1995 |
| WO | WO02/44121 | * | 6/2002 |

OTHER PUBLICATIONS

Aldrich, Catalog Handbook of Fine Chemicals ; p. 811, 1998-1999.*

* cited by examiner

*Primary Examiner*—Taylor Victor Oh
(74) *Attorney, Agent, or Firm*—Jackson Walker L.L.P.

(57) ABSTRACT

Compounds of formula I

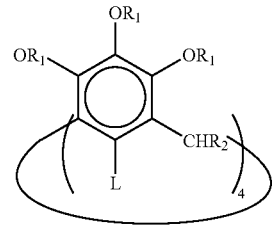

Formula I wherein at least one $R_1$ is H and the remainder are $CH_2CO_2K$; $R_2$ is

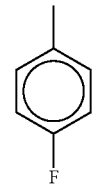

and L is H are described. The compounds are useful as pharmaceutical compositions in the treatment of AIDS.

10 Claims, No Drawings

ANTI-VIRAL COMPOUNDS

FIELD OF THE INVENTION

The present invention relates to compounds having biological activity and to processes for the preparation thereof. The invention is particularly directed to compounds having anti-viral, particularly anti-HIV activity.

BACKGROUND TO THE INVENTION

The virus that causes AIDS, the human immunodeficiency virus HIV is believed to be one of the major threats to human life and health worldwide. Even back in 1988 an article in Scientific American by J. M. Mann, J. Chin, P. Piot and T. Quinn estimated that more than a quarter of a million AIDS cases had occurred in the U.S.A. up to then and that 5-10 million people were infected worldwide. An article in the same magazine ten years later "Defeating Aids: What will it take? (July 1998 page 62) revealed that worldwide 40 million people had contracted HIV and almost 12 million had died leaving over 8 million orphans. During 1997 alone nearly 6 million people acquired HIV and some 23 million perished including 460,000 children.

Although 90% of HIV infected people live in developing countries well over 90% of money for care and prevention is spent in industrial countries. The very expensive triple therapy drugs (over US$10,000-$15,000 per person per year) are well beyond the reach of individuals in developing countries in sub Saharan Africa and Asia. In 1999 alone, 300,000 people died in Ethiopia from AIDS far exceeding deaths from famine (12 Apr. 2000, The Irish Examiner). Up to a quarter of South Africa's non-whites currently face death from AIDS in the next ten years (11 May 2000, The Irish Examiner, by G. Dyer). There is thus a desperate need for cheap, easily made and efficient anti-HIV agents for the developing world.

The HIV has been studied more intensively than any other virus and we now have a general picture of how the genes and proteins in the HIV virus particle operate, although we don't have a clear understanding of what controls the replication and how it destroys the human immune system. There are in fact many strains of HIV. The two main ones are HIV-1 and HIV-2. HIV-2 is prevalent in West Africa and produces a less severe disease than does HIV-1 the most common form elsewhere.

The life cycle of the virus is described below in some detail since for a drug to be effective it has to interfere with at least one stage of its life cycle. The HIV virus particle is roughly spherical shaped and is about a thousandth of a millimeter across. Its outer membrane consists of lipid molecules which possess many viral protein spikes projecting outwards. Each spike is thought to consist of four molecules of glycoprotein gp120 with the same number of glycoprotein gp41 molecules embedded in the membrane itself. These envelope proteins come into play when HIV binds and then enters target cells. Gp120 can bind tightly to CD4 proteins sited in the membranes of immune system cells especially T lymphocytes also called T cells. This is the first stage of the infection which is followed by fusion of the virus and T cell membrane, a process governed by the gp41 envelope protein. The result is that the contents of the virus core are thus freed to enter the cell. The virus core is surrounded by matrix protein called p17 and is itself in the shape of a hollow cone made of another protein p24 containing the genetic material of the virus.

Being a retrovirus this genetic material is in the form of RNA (ribonucleic acid) consisting of two RNA strands. These are in turn attached to molecules of an enzyme, reverse transcriptase, which transcribes the viral RNA into DNA once virus has entered the cell. Coexisting with RNA are an integrase, a protease, a ribonuclease and other enzymes. Once in the cell the viral RNA is converted to DNA which then enters the cell nucleus. The next step is integration of viral DNA into host chromosomes. This is followed by cell proteins binding to DNA initiating transcription. Short RNA molecules then leave the nucleus and make viral regulatory proteins followed by medium length and long RNA which generate structural and enzymatic proteins. These assemble to form new viruses (replication-viral budding) (1).

Prior to 1991 the only drug available to combat HIV/AIDS was Glaxo-Wellcome's AZT (zidovudine) a nucleoside analogue which works by binding to the reverse transcriptase enzyme thereby inhibiting viral replication. Unfortunately, long term use led to the virus developing resistance against the drug by mutation. New drugs in the same class were subsequently developed including 3TC (lamivudine) (Glaxo-Wellcome), ddc (zalcitabine) (Roche), ddI (didanosine)(Bristol-Myers Squibb), d4T (stavudine) (Bristol-Myers Squibb) and recently abacavir (Glaxo-Wellcome).

1996 saw the introduction of a new class of drugs which acted at a different (and later) stage in the HIV virus' life cycle by blocking the action of the protease enzyme during viral replication. Furthermore, use of one of these with two of the class above (reverse transcriptase) gave viral loads in the blood being reduced by up to 4 log units or by a factor of ten thousand. Use of one drug alone reduces viral load by up to 2 log units or by a factor of one hundred. An effective example of this so called triple therapy would be use of AZT and 3TC (reverse transcriptase inhibitors) and indinavir (Merck Sharp and Dohme) or nelfinavir (Agouron) (protease inhibitors). Other protease inhibitors include saquinavir (Roche), ritanovir (Abbott laboratories) and amprenavir (Glaxo-Wellcome). In general, effective therapies employ two reverse transcriptase inhibitors together with one protease inhibitor.

1996 also saw the introduction of another new class of drugs known as non-nucleoside reverse transcriptase inhibitors, the first being nevirapine (Boehringer Ingelheim) followed by delavirdine. (Pharmacia Upjohn) in 1997 then efavirenz (Du Pont) in 1998.

New effective therapies also capable of reducing viral loads by up to 4 log units or by a factor of 10,000 employ a combination of nucleoside and non-nucleoside reverse transcriptase inhibitors using a total of at least three drugs.

The cost of any triple therapy per patient per year is £10,000-£15,000. (2).

The following table gives an overview of current AIDS drugs, their type or class, effectiveness in reducing viral load, total amount of drug given to patient each day in number of doses, side-effects, time for viral drug resistance to develop when used alone, and approximate cost per patient per year. (2).

The first mentioned nucleoside reverse transcriptase enzyme inhibitor zidovudine (AZT) when used by itself has subsequently been shown to provide no benefits in treating HIV-infected individuals (3) although it is effective reducing transmission from mother to baby (4).

However, it can be effective when used in conjunction with other AIDS drugs such as 3TC, another nucleoside reverse transcriptase enzyme inhibitor (5).

Additionally, the HIV virus develops viral drug resistance against AZT rather quickly (5-6 months) when used alone and even more rapidly (1 and a half months) against 3TC when used alone (2). All nucleoside revere transcriptase enzyme inhibitors can cause serious side effects ranging from myopathy to peripheral neuropathy (nerve damage). The most recent drug abacavir's side effects can be life-threatening so treatment with this drug is immediately stopped at the first signs of any adverse reactions. Also ddc is a very toxic drug. Reduction in viral loads by drugs used on their own are only moderate 50-90% and their cost is quite high (£1,200-£10,000 per patient per year) (2).

The relatively recently developed non-nucleoside reverse transcriptase enzyme inhibitor AIDS drugs can cause severe skin reaction in patients and the HIV virus can develop viral drug resistance against them very quickly in 2 months in monotherapy (one drug). In addition, cross viral drug resistance has been noted using this class of drugs. In this case drug resistance against one drug in the class can cause drug resistance against another drug of the same class (2). Again used by themselves they only reduced viral load in patients by 50-90% and are relatively expensive (£1800-£2400 per person per year) (2).

The new protease enzyme inhibitors have to be given to patients in relatively large amounts (1250-2400 mg per clay) and can give serious side effects ranging from kidney stones to hepatitis and after prolonged use patients exhibit raised levels of cholesterol and triglycerides and can cause diabetes and abnormal distribution of body fat. In addition they are expensive (£4000-£7000 per person per year) (2). They are also generally poorly absorbed and have poor bioavailability which could well be related to their low water solubility (6), (Protease Inhibitors in Patients with HIV disease by M. Barry, S. Gibbons, D. Back and F. Mulcahy in Clinical Pharmacokinetics March 32 (3) 1997 p 194) and can interact with other protease enzyme inhibitors and nucleoside/non-nucleoside enzyme inhibitors in combination therapy, giving rise to a very strict order of oral dosing which must be adhered to by the patient (7) (Pharmacokinetics and Potential Interactions amongst Antiretroviral Agents used to treat patients with HIV infection by M. Barry, F. Mulcahy, C. Merry, S. Gibbons and D. Back, Clinical Pharmacokinetics, April 36(4) 1997 p 289).

| | | | MARKETPLACE COMPARISON | | | |
|---|---|---|---|---|---|---|
| DRUG | TYPE | REDUCTION IN VIRAL LOAD | TOTAL AMOUNT DRUG/DAY in (x) doses | SIDE EFFECTS | VIRAL DRUG RESISTANCE (MTHS) | COST/ PATIENT/ YEAR (PUNTS) COMPANY |
| Zidovudine (AZT) | nucleoside reverse transcriptase inhibitor | 50–90% | 600 mg (2) | myelosupression, myopathy, nausea, headache, anaemia | 5–6 | £7,000–£10,000 Glaxo-Wellcome |
| Lamivudine (3TC) | nucleoside reverse transcriptase enzyme inhibitor | 50–90% | 300 mg (2) | gastrointestinal disturbances, hair loss, myelosuppression, exacerbation of peripheral neuropathy | 1½ | £7,000 Glaxo-Wellcome |
| Stavudine (d4T) | nucleoside reverse transcriptase enzyme inhibitor | 50–90% | 40 mg (2) | peripheral neuropathy | greater than 6 | £1,800 Bristol Myers Squibb |
| Didanosine (ddl) | nucleoside reverse transcriptase enzyme inhibitor | 50–90% | 300–400 mg (1) (at night) | peripheral neuropathy, nausea vomiting, pancreatis | greater than 6 | £2,000 Bristol Myers Squibb |
| Zalcitabine (ddc) | nucleoside reverse transcriptase enzyme inhibitor | 50–90% | 0.75 mg (1) (with meals) | very severe peripheral neuritis | greater than 6 | £1,200 Roche |
| Abacavir | nucleoside reverse transcriptase enzyme inhibitor | 50–90% | 300 mg (2) | any reaction can be life-threatening always stopped immediately | — | £2,400 Glaxo-Wellcome |
| Nevirapinc | non-nucleoside reverse transcriptase enzyme inhibitor | 50–90% | 200 mg (2) | skin reaction | 2 | £1,800 Boehringer Ingelheim |
| Delaviridine | non-nucleoside reverse transcriptase enzyme inhibitor | 50–90% | 600 mg (3) many tablets | skin reaction | 2 | £1,800 Pharmacia-Upjohn (Agouron) |

-continued

MARKETPLACE COMPARISON

| DRUG | TYPE | REDUCTION IN VIRAL LOAD | TOTAL AMOUNT DRUG/DAY in (x) doses | SIDE EFFECTS | VIRAL DRUG RESISTANCE (MTHS) | COST/ PATIENT/ YEAR (PUNTS) COMPANY |
|---|---|---|---|---|---|---|
| Efavirenz | non-nucleoside reverse transcriptase enzyme inhibitor | 50–90% | 600 mg (1) | skin reaction | 2 | £2,400 Dupont |
| Indinavir | protease enzyme inhibitor | 99% | 2400 mg (3) | hyperbilirubinaemia, nephrolthiasis, nausea, kidney stones, dizziness | 6 | £5,000–£7,000 Merck Sharp & Dohme |
| Ritonavir (not used by itself) | protease enzyme inhibitor | 99% | 1800 mg (2) | diarrhoea nausea, vomiting, hepatitis, headache | 6 | £5,000–£7,000 Abott Laboratories |
| Saquinavir | protease enzyme inhibitor | 99% | 1800 mg (2) | loose stools, nausea, headache | 6 | £5,000–£7,000 Roche |
| Nelfinavir (Viracept) | protease enzyme inhibitor | 99% | 1250 mg (2) a lot of tablets total 10 | diarrohea, nausea & vomiting | 6 | £4,000–£5,000 Agouron (Roche) |
| Amprenavir (can be used with Ritonavir) | protease enzyme inhibitor | 99% | a lot of tablets | severe rash | — | £7,000 Glaxo-Wellcome |

All protease enzyme inhibitors raise patient's cholesterol, triglyceride levels and can cause diabetes, kidney stones and abnormal distribution of body fat after prolonged use.

The concentration at which an HIV-1 drug is effective is designated $EC_{50}$ μm which represents when the number of cells protected from HIV injection is half the total. The antigen Agp120 assay—the virus related antigen—is related to the number of virus particles produced by measuring glycoprotein gp120 in infected cell cultures. The concentration of the drug which reduces cell growth by 50% is designated $TC_{50}$ μM.

Of course the lower the $EC_{50}$ concentration the better but the real criterion of effectiveness in in vitro testing on cell cultures is the Therapeutic index which is the $TC_{50}/EC_{50}$ ratio. The therapeutic index is selected so as not to damage healthy cells. Thus AZT has an $EC_{50}$ of ca 0.016 μM with a $TC_{50}$>1000 μM. This results in a therapeutic index of >1000/0.016=>62,500. This figure serves as a benchmark against which new potential drugs can be measured. Of course human beings and animals are more than a collection of cells and in spite of the high Therapeutic Index, AZT is quite toxic, giving rise to nerve damage and anaemia among other things (2). Nevertheless, such tests on cell cultures indicate what is a potential anti-HIV drug.

Other factors relevant to the usefulness of an anti-HIV drug are physical properties such as water-solubility for drug absorption by the patient and stability of the compound after oral intake. Thus the potentially useful drug, the anionic polysaccharide, dextran sulphate is poorly absorbed orally and degrades after oral intake before entry into the plasma (8). Another important factor is the ease of synthesis of the drug and hence drug cost which is relatively high for AZT and most other drugs produced to date which are potentially useful in combating AIDS.

International Publication No. WO9403164 describes compounds having biological activity, particularly sulfonate based calixarenes, having anti-HIV activity.

International application No. PCT/IE01/00150 relates to compounds selected from the general group of compounds disclosed in international publication no. WO 95/19974 having especially surprising activity. It relates in particular to cyclic tetrameric pyrogallol-aldehyde derivatives and to calixarene derivatives which are useful in the treatment of AIDS. In particular, International application No. PCT/IE01/00150 discloses the dodecapotassium acetate of p-bromopyrogallol P—F-phenyl tetramer (AC-1 (Example 1 in PCT/IE01/00150)).

Further studies have been flied out on synthetic routes for AC-1 which demonstrate, rather surprisingly, that a non-brominated, partially alkylated analogue of AC-1 may be more active as an anti-AIDS drug than AC-1.

International Application No. PCT/IE01/00150 and International Publication No. WO 95/19974 do not teach the formation of a partially alkylated, non-brominated analogue of AC-1. Indeed, the problems associated with the complex step of selective alkylation during the synthesis of the compound disclosed herein teach away from the formation of a partially alkylated compound. In particular, the present invention relates to a tetra-alkylated non-brominated analogue of AC-1.

The present application also relates to the use of this non-brominated, partially alkylated compound in a pharmaceutical composition for the treatment of HIV-1.

There is a need for an anti-HIV drug which brings about a reduction in viral load but without causing the development of viral drug resistance and problems of toxicity. In short, a drug is needed which when given orally gives rise to at least a M.I.C. (Minimum inhibitory concentration) of drug in the blood against HIV but at a low enough concentration so as not to give rise to adverse side effects in the patient.

OBJECT OF THE INVENTION

It is an object of the present invention to provide novel and easily synthesised compounds having biological activity, particularly anti-HIV activity, particularly against HIV-1.

It is another object of the invention to provide a partially alkylated pyrogallol P—F-phenyl tetramer for use as an anti-Aids or anti-HIV agent.

It is a further object of the invention to provide compounds having a low $EC_{50}$ or MIC in patients blood (plasma) concentration which exhibit reduced and preferably little or no side effects, and bring about a reduction in viral load but without causing the development of viral drug resistance and pharmaceutical compositions thereof.

SUMMARY OF THE INVENTION

The invention provides compounds of formula I

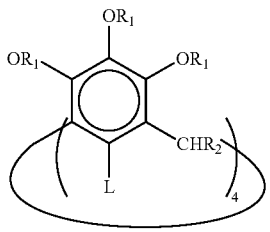

Formula I wherein at least one $R_1$ is H and the remainder are $CH_2CO_2K$; $R_2$ is

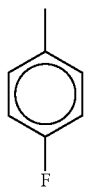

and L is H.

The invention also provides compounds of formula I where 4 to 8 of $R_1$ are $CH_2CO_2K$, the remaining $R_1$ substituents are H, $R_2$ is

and L is H.

In one embodiment the invention provides a mixture of compounds of formula I having different degrees of alkylation. For example a mixture of compounds comprising tetra-alkylated and penta-alklyated compounds of formula I may be provided. Similarly, mixtures of compounds having between 6 and 8 alkyl groups may be provided.

In a preferred embodiment, the invention provides a compound of formula II

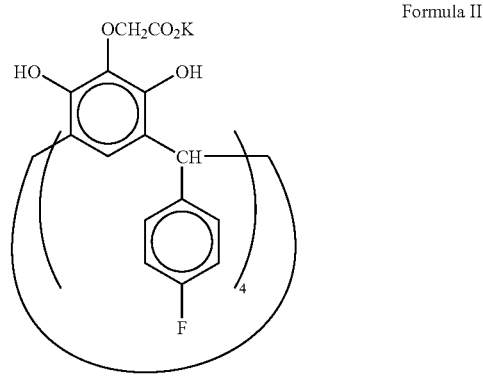

Formula II

The compounds of formula I or II of the invention may be used in the preparation of a medicament for the treatment of viral infection, particularly HIV-1 infection.

The invention further provides a pharmaceutical composition comprising a pharmaceutically effective amount of a compound of formula I or II. The pharmaceutical composition may comprise at least one compound of formula I or II. The compounds of the present invention may be used in combination with pharmaceutically acceptable carriers or diluents to form pharmaceutical compositions for the treatment of viral infections, particularly HIV-1 infection.

In addition, the compounds according to the invention and in particular, mixtures of compounds of formula I having different degrees of alkylation may be used in combination with pharmaceutically acceptable carriers or diluents to form pharmaceutical compositions for the treatment of secondary infections/conditions associated with HIV-1 infection, as, well as the treatment of HIV-1 infections themselves.

The invention also provides for the use of compounds of formula I or II or a mixture of compounds of formula I; having different degrees of alkylation, together with an anti-viral agent in the preparation of a medicament for the treatment of viral infection, particularly HIV-1 infection. The tables below list examples of anti-viral agents that may be used.

| Currently approved antiretrovirals (US FDA) | | |
|---|---|---|
| Revers Transcriptase Inhibitors | | |
| NRTI | NNRTI | Protease Inhibitors |
| Retrovir (zidovudine: AZT) | Virammune (nevirapine) | Fortovase and Invirase (saquinavir) |
| Epivir (lamivudine; 3TC) | Rescriptor (delaviridine) | Norvir (ritonavir) |
| Combivir (AZT + 3TC) | Sustiva (efavirenz) | Crixivan (indinavir) |
| Hivid (zalcitabine; ddC) | | Viracep (nelfinavir) |
| Videx (didanosine; ddI) | | Ageberase (aprenavir) |
| Trizivir (abacavir + AZT + 3TC) | | Kaletra (lopinavir + nitonavir) |
| Zeril (starvudine, D4T) | | |
| Ziagen (abacavir) | | |
| Vired (tenofovit) | | |

| Investigational antiretrovirals | | |
|---|---|---|
| Target | Inhibitor | Comments |
| HIV entry | | |
| Virus-cell Interaction | Soluble CD4 | |
| | Toxin conjugated CD4 | |
| | Mab to CD4 or gp120 | |
| | PRO 542 | Progenics Pharmaceuticals/GTC Biotherapies |
| | Dextran sulphate | |
| | Rersobene | |
| | FP-23199 | |
| | Cyanovirin-N | |
| | Zintevir (T30177, AR177) | |
| | L-chicoric acid derivatives | |
| Coreceptor Inhibitors Ligands | R5 | |
| | X4 | |
| | Modified ligands (R5) | |
| | Modified Ligands (X4) | |
| Coreceptor Inhibitors X4 | T22, T134 | |
| | ALX40-C | |
| | AMD3100 | |
| | Bicyclam derivatives | |
| Coreceptor Inhibitors R5 | TAK-779 | |
| | SCH-C(SCH-351125) | |
| | SCH-D(SCH-350634) | |
| | NSC 651016 | |
| | ONO Pharmaceutical | |
| | Merck (Fusion inhibitors) | |
| Fusion Inhibitors | Fuzeon (T-20, DP 178, enfuvritide) | Roche/Trimeris |
| | T-1249 | Roche/Trimeris |
| | TMC125 | Tibotec |
| Integrase Inhibitors | 5CITEP | |
| | L731,988 | |
| | L708,906 | |
| | L-870,812 | |
| | S-1360 | |
| NCp7nucleocapsid Zn finger inhibitors | NOBA | |
| | DIBA | |
| | Dithianes | |
| | PD-161374 | |
| | Pyridinioalkanoyl thioesters (PATES) | |
| | Azodicarbonamide (ADA) | |
| | Cyclic 2,2 dithio bisbenzamide | |
| RT Inhibitors | | |
| NRTI | Coviracil (emtricitabine) | Triangle Pharmaceuticals |
| | DAPD (amdoxivir) | Triangle Pharm. |
| NNRTI | GW687 | |
| | DPC083 | |
| | TMC 125 | Tibotec |
| | Emivirine | |
| | Capravirine | |
| | BMS 561390 | BMS |
| | UC-781 | |
| | (and other oxathiin carboxanilides) | |
| | SJ-3366 | |
| | Alkenyldiarylmethane (ADAM) | |
| | Tivirapine | |
| | Calanolide A | Sarawak MediChem Pharmaceuticals |
| | HBY097 | |
| | Loviride | |
| | HEPT family derivatives | |
| | TIBO Derivatives | |
| RNase H inhibitors | BBHN | |
| | CPHM | |
| | PD-26388 | |
| Protease Inhibitors | Atazanavir (BMS-232632) | BMS |
| | Tipranavir | Boehringer Ingleheim |
| | DMP450 | |
| Tat inhibitors | Dominant negative mutants | |
| | Ro24-7429 | |
| | Ro5-3335 | |
| Rev inhibitors | Dominant negative mutants | |
| | Leptomycin E | |
| | PKF050-638 | |

-continued

| Investigational antiretrovirals | | |
|---|---|---|
| Target | Inhibitor | Comments |
| Transcriptional Inhibitors | Temacrazine K-12 and K-37 EM2487 | |
| Virus assembly/ Maturation | CAP-1, CAP-2 | |
| Cellular anti-HIV Targets | LB6-B275, HRM1275 Cdk9 inhibitors | |

Further, the pharmaceutical composition according to the invention may comprise a compound of the invention together with a pharmaceutically effective carrier or excipient, and may be formulated as an injectable solution, a tablet, capsule, suppository or as a cream, gel or ointment for topical application.

The invention also provides a method of treatment of HIV infection comprising administering to a patient a pharmaceutically effective amount of at least one compound of formula I or II.

Further, the invention provides a method of treatment of infection comprising administering to a patient a pharmaceutically effective amount of at least one compound of formula I or II or a mixture of compounds of formula I having different degrees of alkylation. The compounds may be administered together with an anti-viral agent.

The invention will be described in greater detail with reference to the following examples.

DETAILED DESCRIPTION OF THE INVENTION

The present invention relates to non-brominated, partially alkylated pyrogallol calixarene type compounds and derivatives thereof. The compounds according to the invention may be prepared by selective alkylation of the cyclised calixarene type compound of the following formula

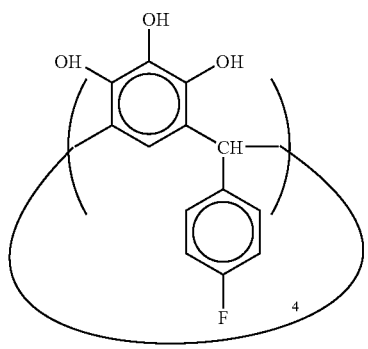

The difficulties associated with selective alkylation of cyclised calixarenes of the above formula will be appreciated by those skilled in the art. In particular, in the above cyclised calixarene there are twelve hydroxyl groups. Esterification can take place at twelve reaction sites. Some of the reaction sites are less reactive than others due to possible steric hindrance. It will be appreciated by those skilled in the art that several of the hydroxyl groups in the non-alkylated calixarene are hindered which could prevent alkylation occurring at these positions. Once the first alkyl group is alkylated the steric is hindrance is increased. Thus it will be further appreciated by those skilled in the art that such steric hindrance may prevent total alkylation occurring unless vigorous conditions are applied such as, for example, stirring under reflux for 72 hours using a large excess of alkylating agent. Thus following alkylation, the product can contain between 1 and 11 alkyl substituents.

It will further be appreciated by those skilled in the art that partially alkylated compounds such as those described herein may be prepared by selective alkylation incorporating the use of well known protecting groups.

Table 1 shows the activity of compounds which were prepared in the following examples and tested.

EXAMPLE 1

Preparation of Compound BC130202A

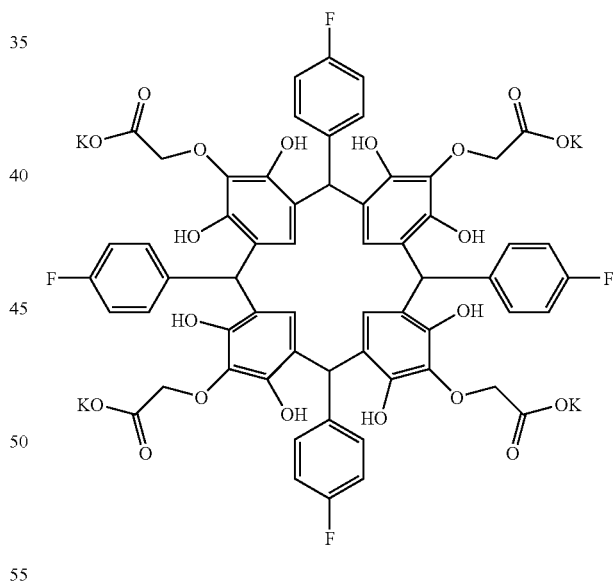

(i) Preparation of Pyrogallol Calixarene:

To pyrogallol (40 g, 0.317 mole) in absolute ethanol (180 cm$^3$) was added p-fluorobenzaldehyde (39 g, 0.317 mole) and 37% HCL $_{(aq.)}$(46.5 cm$^3$). The reaction mixture was stirred under reflux for five hours. After cooling, the solid precipitate was collected by filtration and washed with ethanol: water (4:1). The crude brown solid was then slurried under reflux in methanol, cooled, filtered and washed with cold methanol to yield 39 g (53%) of a grey/white solid.

(ii) Pyrogallol calixarene (14 g, 0.015 mole) was treated with potassium carbonate (12.44 g, 0.09 mole) and ethylbromoacetate (15.03 g, 0.09 mole) in acetone (150 cm³). The reaction mixture was stirred at room temperature under a nitrogen atmosphere for seventy-two hours. The solvent was evaporated under vacuum and the residue treated with ca 2N HCl $_{(aq)}$ (100 cm³). The resultant brown solid was slurried in methanol to yield a brown coloured solid (8.26 g, 43%).

(iii) The tetra-alkylated pyrogallol calixarene (6 g, 0.005 mole) in absolute ethanol (50 cm³) was treated with KOH (6.6 g, 0.12 mole). The reaction mixture was stirred under reflux for two hours and filtered hot. The brown solid was washed with hot ethanol and dried in the oven to yield the product (7.26 g, 100%).

EXAMPLE 2

Preparation of BC010302B

Pyrogallol calixarene was prepared as outlined in Example 1 (i). Pyrogallol calixarene was then alkylated in accordance with the procedure outlined in Example 1 (ii) except six equivalents of ethylbromoacetate and potassium carbonate were used. Alkylation was carried out under reflux for three days. A mixture of compounds was obtained (BC010302B).

EXAMPLE 3

Preparation of BC010302B

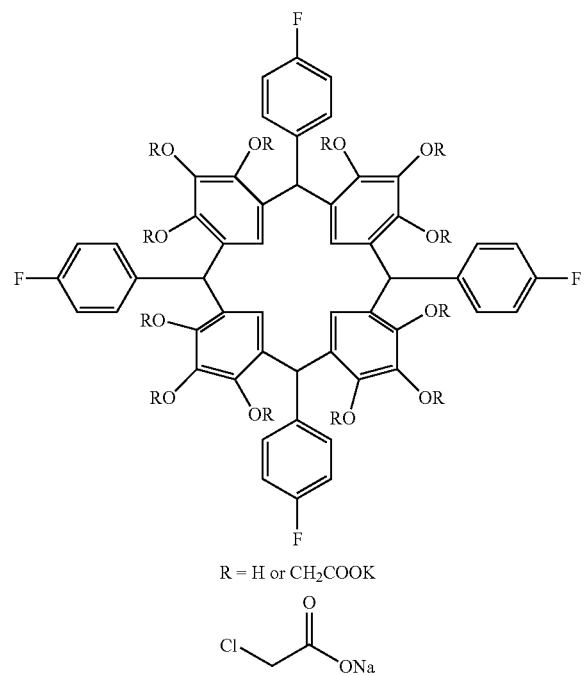

Pyrogallol calixarene was prepared as outlined above in Example 1 (i). Pyrogallol calixarene (9.30 g, 0.01 mole) in acetone (100 cm³) was treated with potassium carbonate (11.05 g, 0.08 mole) and chloroacetic acid (7.5 g, 0.08 mole) in acetone (50 cm³) added drop wise. The reaction mixture was stirred at room temperature under a nitrogen atmosphere over night. The solution was filtered, washed with acetone, slurried in methanol and acidified with conc. HCl. The solid was then slurried in ethanol and treated with KOH under reflux for 30 minutes to convert to the potassium salt. The solid was filtered and dried in a vacuum oven to yield 6.4 g of material.

EXAMPLE 4

Preparation of BC070202A

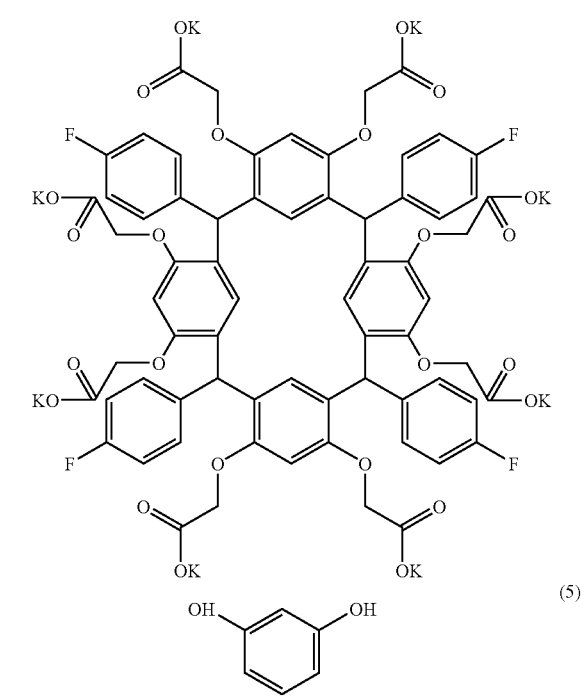

(i) To resorcinol (5) (10 g, 0.091 mole) in absolute ethanol (40 cm³) was added p-fluorobenzaldehyde (11.3 g, 0.091 mole) and 37% HCl $_{(aq.)}$(13.5 cm³). The reaction mixture was stirred under reflux for five hours. After cooling, the solid precipitate was collected by filtration and washed with ethanol: water (4:1). The crude brown solid was then slurried under reflux in methanol, cooled, filtered and washed with cold methanol to yield 11.3 g (53%) of a grey/white solid.

(ii) Alkylation.

Resorcarene (4 g, 0.0046 mole) was treated with potassium carbonate (6.4 g, 0.046 mole) and ethylbromoacetate (7.72 g, 0.046 mole) in acetone (50 cm³). The reaction mixture was stirred at room temperature under a nitrogen atmosphere for seventy-two hours. The solvent was evaporated under vacuum and the residue treated with ca 2N HCl $_{(aq)}$ (30 cm³). The resultant brown solid was slurried in methanol to yield an off white coloured solid (63 g, 87% o).

(iii) Hydrolysis

The alkylated resorcarene (6 g, 0.004 mole) in absolute ethanol (40 cm³) was treated with KOH (5.61, 0.1 mole). The reaction mixture was stirred under reflux for two hours and filtered hot. The white solid was washed with hot ethanol and dried in the oven to yield the product (6.31 g, ca. 100%).

EXAMPLE 5

Preparation of

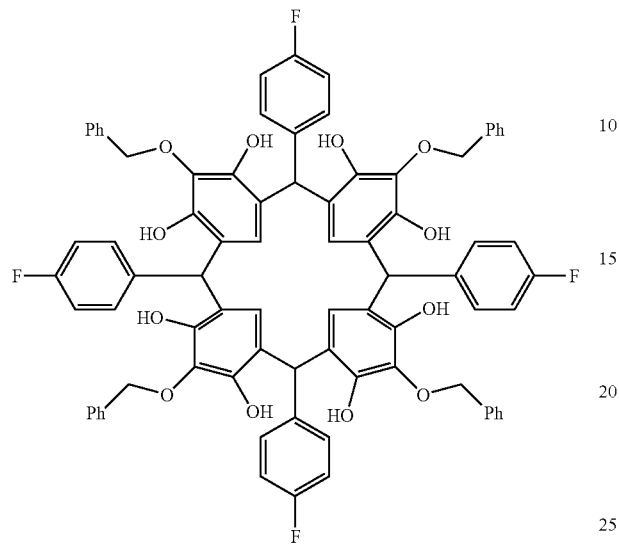

It will be appreciated by those skilled in the art that the above tetra-benzyl product could be prepared by a process analogous to Example 2 above.

EXAMPLE 6

Preparation of

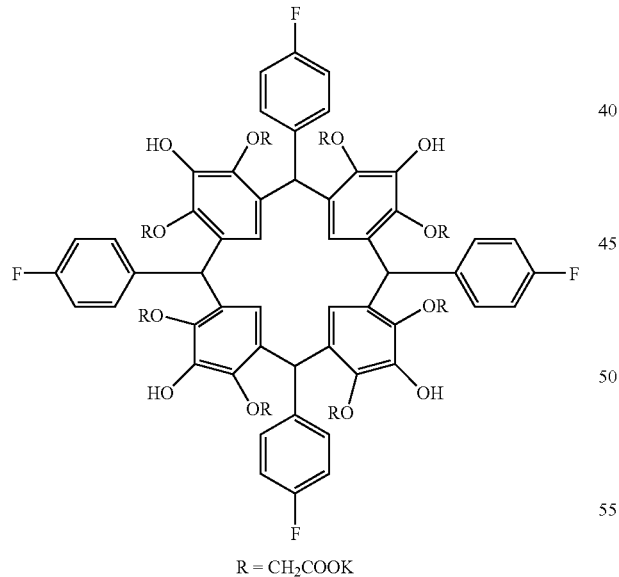

R = CH$_2$COOK

The above compound may be prepared by fully alkylating the tetra-benzyl product of Example 5 and then deprotecting by removing the benzyl groups and alkylating to form the above octa-alkyl product.

It will be appreciated by those skilled in the art that pre-alkylated pyrogallol such as shown below may be reacted with p-fluorobenzaldehyde to yield a definitive calixarene structure.

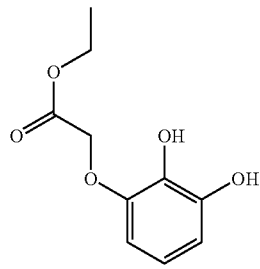
(12)

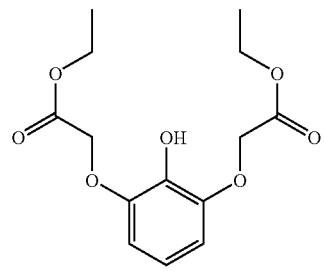
(13)

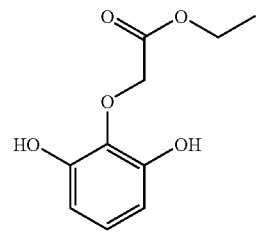
(14)

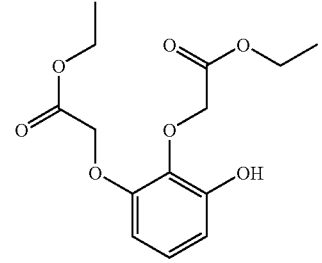
(15)

4-Possible alkylated Pyrogallol substructures

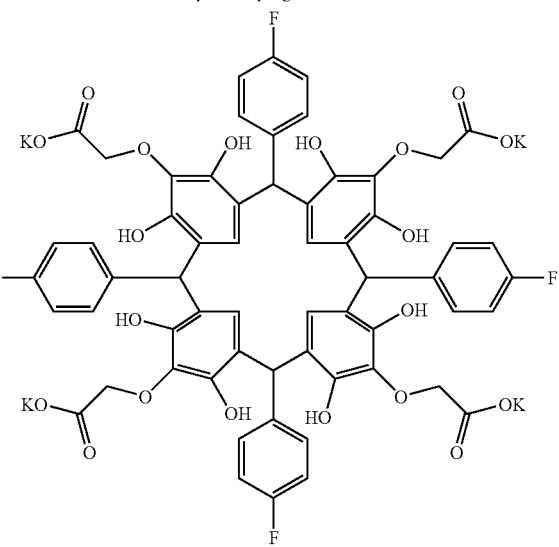

To prove the structure of the tetra-alkyl product shown above pre-alkylated pyrogallol intermediates for cyclisation are prepared. The intermediate (6) on cyclisation with 4-fluorobenzaldehyde can produce the tetra-alkyl ester, which on hydrolysis yields the tetra-alkyl product shown above.

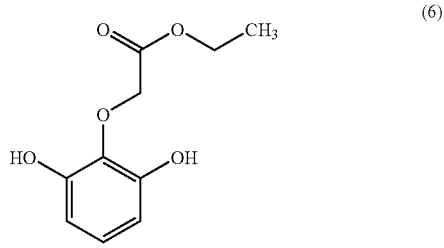

(6)

Other possible products are analogous tetra-alkyl products (7). Preparation of these products requires the preparation of alternative tetramers using alternatives to 5-fluorobenzaldehyde. Based on the precedent already established, selective tetra-alkyation takes place. Alternatively, the alkylating agent can be varied to produce analogous products, to probe the activity requirement of the alkyl groups.

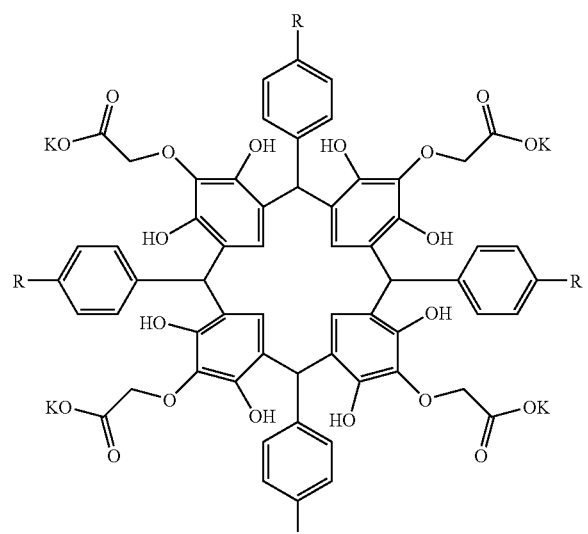

R = H, Br, Cl, OMe etc.
Tetra-alkyl product analogues (7)

Clinical Results

Anti-HIV Activity

Determination of $EC_{50}$ and $TC_{50}$

Antiviral Assays

The concentration at which an HIV-1 drug is effective is designated $EC_{50}$ μm which represents when the number of cells protected from HIV injection is half the total. The antigen Agp120 assay—the virus related antigen—is related to the number of virus particles produced by measuring glycoprotein gp 120 in infected cell cultures. The concentration of the drug which reduces cell growth by 50% is designated $TC_{50}$ μM.

Of course the lower the $EC_{50}$ concentration the better but the real criterion of effectiveness in in vitro testing on cell cultures is the Therapeutic index which is the $TC_{50}/EC_{50}$ ratio.

gp 120 Antigen Assay

A microtiter antigen capture ELISA was developed using lectin (GNA) from *Galanthus nivalis* (Vector Laboratories, Peterborough, UK.) and human antibodies (10). The plates were coated with lectin (0.5 ug), and after blocking with 10% calf serum, dilutions of virus supernatant in 0.25% detergent solution (Empigen, Albright and Wilson Ltd., Whitehaven, UK.) were added to the wells and incubated at 4° C. for 12-16 hours. Bound antigen was captured using human anti-HIV antibodies, and finally detected with anti-human Ig antibodies conjugated to horseradish peroxidase.

A selection of compounds prepared in accordance with the preceding examples were tested and compared with an original sample of AC-1 (1151c). Two tests were performed: Test 1 was performed using infected blood, while Test 2 used cell cultures. The results are shown in Table 1 which illustrates the activity of the compounds tested.

TABLE 1

AC-1 (1151c) structure: $R = CH_2CO_2K$

| Compound | Description | Molecular Weight | Test 1 $EC_{50}$ (μM) | Test 2 $EC_{50}$ (μg/ml) |
|---|---|---|---|---|
| AC-1 (1151c) | Original Compound AC-1* | 1850.2 | 0.5-1.0 | 4 |
| BC010302B | Mixture of partially alkylated compounds of Formula I | 1792.6 | 1.25 | 8 |
| BC130202A | Tetra-alkylated compound | 1618.0 | 5.0 | 10 |
| BC010302A | Partially alkylated compound of Formula I | 1850.2 | 4-8(6) | ≧40 |
| BC070202A | Resorcarene | 1633.8 | 75.0 | ≧20 |

*corrected molecular weight

The results from both tests were comparable. The activity of BC010302B was comparable to that of the sample of AC-1 (1151c). The tetra-alkylated compound BC130202A was also active, demonstrating an $EC_{50}$ of 5 μM.

Of the two pure compounds, the AC-1 analogue BC130202A was slightly less active than the compound AC-1, while the resorcarene was much less active than the compound AC-1 (1115c).

TABLE 2

| Compound | Conc um | % inhibition of gp120/CD4 binding |
|---|---|---|
| 1151C | 100 | 96 |
| | 50 | 93 |
| | 25 | 91 |
| | 12.5 | 86 |
| | 6.25 | 82 |
| | 3.125 | 70 |
| | 1.56 | 62 |
| | 0.78 | 55 |
| | 0.39 | 48 |
| BC010302A | 100 | 80 |
| | 50 | 72 |
| | 25 | 60 |
| | 12.5 | 55 |
| | 6.25 | 42 |
| | 3.125 | 34 |
| BC010302B | 100 | 92 |
| | 50 | 88.5 |
| | 25 | 86 |
| | 12.5 | 76 |
| | 6.25 | 67 |
| | 3.125 | 54 |
| | 1.56 | 50 |
| | 0.78 | 44 |
| BC070202A | 100 | 54 |
| | 50 | 31 |
| | 25 | 24 |
| | 12.5 | 24 |
| BC130202A | 100 | 90 |
| | 50 | 82 |
| | 25 | 70 |
| | 12.5 | 56 |
| | 6.25 | 46 |
| | 3.125 | 32 |
| | 1.56 | 19 |

$EC_{50}$ represents the concentration which reduces the viral envelope protein gp120 interaction with the cellular receptor protein CD4 by 50% using recombinant proteins in an immunoassay format.

It has been shown that 1151c (AC-1) type compounds inhibit infection at an early stage of virus infection. This was confirmed by using recombinant proteins for the viral envelope and the cellular receptor. The proteins bind well in vitro using CD4 bound to plastic wells of 96 well plates. The results in the above table were obtained by carrying out the following procedure.

All stocks solutions were made 25 mM in distilled water and tested at same concentrations.

The procedure was carried out as follows:

1 Plastic plates were coated with cellular receptor protein CD4.
2 The plates were washed well before adding a predetermined, appropriate quantity of viral envelope protein gp120 for binding to CD4.
3 To see inhibition by compounds, different concentrations were added a few minutes before adding gp120.
4 The mixture was incubated at 37° C. for binding.
5 The plates were then flashed well and bound gp120 was detected by reaction with anti-HIV antibodies, incubated for 12 hours at 4° C.
6 The amount of antibody bound was detected by adding anti-Human antibodies attached to an enzyme horse raddish peroxidase.
7 After another incubation and wash, the quantity of the enzyme was measured by adding substrate o-phenyl diamine (OPD).
8 The colour developed was read at 492 nm.
9 All incubations took three days for adding different reagents. The percentage of inhibition by compounds, was calculated from the standard curve obtained by using different dilutions of gp120 alone.

Test 2

The results shown in Table 1 for test 2 were obtained by testing cell cultures in accordance with the following procedure.

CEM cells were suspended at approximately 250,000 cells per milliliter of culture medium and infected with wild-type HIV-1 ($111_a$) at approximately 100 times the 50% cell culture infective dose ($CCID_{50}$) per milliliter. Then 100 µl of the infected cell suspensions were added to 200 µl microtiter plate wells containing 100 µl of an appropriate dilution of the test compounds. After 4 days incubation at 37° C. the cell cultures were microscopically examined for syncytium formation. The $EC_{50}$ (50% effective concentration) was determined as the compound concentration required to inhibit syncytium formation by 50%.

The results above demonstrate that a partially alkylated product compound as defined herein, in particular a tetraalkyl product of formula I or a product of formula I containing 6 to 8 alkyl groups is required in order for the compound to be active. It will be appreciated by those skilled in the art that a partially alkylated product may be prepared by conducting selective alkylation under suitable reaction conditions.

The words "comprises/comprising" and the words "having/including" when used herein with reference to the present invention are used to specify the presence of stated features, integers, steps or components but does not preclude the presence or addition of one or more other features, integers, steps, components or groups thereof.

REFERENCES

1. AIDS and the Immune System by W. C. Greene Scientific American 1993 p 67.
2. Drug Cocktails Fight HIV by L. Gopinath, Chemistry in Britain June 1997 p 38 and personal communications from Dr. Sam McConkey, Senior lecturer, Department of Medicine, Oxford University, United Kingdom and Dr. Peter Mugyenyi, Director Joint Clinical Research Centre, Kampala Uganda.
3. AZT Benefit in Doubt, Chemistry in Britain, May 1993, p 62.
4. Defeating AIDS: What will it take?, Scientific American, July 1998, p 62.
5. Potential Mechanism for Sustained Antiretro-viral Efficacy of AZT-3TC Combination Therapy by B. A. Larder, S. D. Kemp and P. R. Harrigan. Science vol. 269, 4 Aug. 1995, p 696.
6. Protease Inhibitors in Patients with HIV Disease by M. Barry, S. Gibbons, D. Back and F. Mulcahy in Clinical Pharmacokinetics, March 32 (3) 1997 p 194.
7. Pharmacokinetics and Potential Interactions amongst antiretroviral agents used to treat patients with HIV infection by M. Barry, F. Mulcahy, C. Merry, S. Gibbons and D. Back, Clinical Pharmacokinetics, April 36(4) 1999 p 289.
8. Molecular Targets for AIDS therapy by H. Mitsuya, R. Yarchoan and S. Broder, Science 28 Sep. 1990 p 1533.
9. N. Mahmood, A. J. Hay (1992) An ELISA utilizing immunobilised snowdrop lectin GNA for the detection of envelope glycoproteins of HIV and SIV. J. Immunol Methods 151:9-13.
10. R. Pauwels, J. Balazarini, M. Baba, R. Snoeck, D. Schols, p. Herdewijn, J. Desmyter and E. De Clerq, (1988) Rapid and automated tetrazolium based colorimetric assay for the detection of anti-HIV compounds. J. Virol Methods 20:309-321.

The invention claimed is:

1. Compounds of formula I

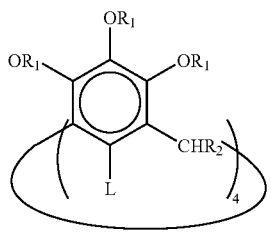
Formula I wherein the compounds are not fully alkylated, in that at least one $R_1$ group is H and the remaining entire 11 or fewer of 11 $R_1$ groups are $CH_2CO_2K$, and wherein the compounds are partially alkylated, in that at least one $R_1$ group is $CH_2CO_2K$; $R_2$ is

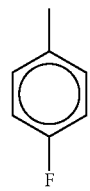

and L is H.

2. A compound of formula I as claimed in claim 1 where 4 to 8 of $R_1$ are $CH_2CO_2K$, the remaining $R_1$ substituents are H, $R_2$ is

and L is H.

3. A compound of formula II

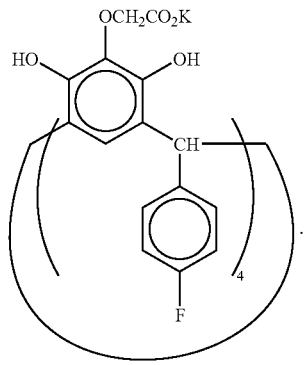
Formula II

4. A mixture of compounds of formula I of claim 1, wherein the compounds have different degrees of alkylation in that the number of $R_1$ groups that are $CH_2CO_2K$ independently ranges from 1 to 11 for each compound in the mixture.

5. A pharmaceutical composition comprising a pharmaceutically effective amount of a compound of formula I of claim 1 or formula II of claim 3, together with a pharmaceutically acceptable carrier or diluent.

6. A pharmaceutical composition comprising a pharmaceutically effective amount of a mixture of compounds according to claim 4, together with a pharmaceutically acceptable carrier or diluent.

7. A pharmaceutical composition comprising a pharmaceutically effective amount of a compound as claimed in any one of claims 1 to 3 or a mixture as claimed in claim 4, together with an anti-viral agent and a pharmaceutically acceptable carrier or diluent.

8. A method of treatment of HIV-1 infection comprising administering to a patient a pharmaceutically effective amount of at least one compound of formula I of claim 1 or formula II of claim 3.

9. A method of treatment of HIV-1 infection comprising administering to a patient a pharmaceutically effective amount of a mixture of compounds of formula I of claim 1 wherein the compounds have different degrees of alkylation in that the number of $R_1$ groups that are $CH_2CO_2K$ independently ranges from 1 to 11 for each compound in the mixture.

10. A method of treatment of HIV-1 infection comprising administering to a patient a pharmaceutically effective amount of at least one compound of formula I of claim 1 or formula II of claim 3 or a mixture of compounds of formula I of claim 1 wherein the compounds have different degrees of alkylation in that the number of $R_1$ groups that are $CH_2CO_2K$ independently ranges from 1 to 11 for each compound in the mixture, together with an anti-viral agent.

* * * * *